United States Patent
Fladda et al.

(10) Patent No.: US 6,777,201 B1
(45) Date of Patent: Aug. 17, 2004

(54) METHOD FOR THE DETERMINATION OF THE CONCENTRATION OF MICRO-ORGANISMS

(75) Inventors: Gerdt Fladda, Täby (SE); Stig Norder, Säffle (SE); Helena Bergsland, Säffle (SE)

(73) Assignee: BTG Kalle Inventing AB, Saffle (SE)

( * ) Notice: Subject to any disclaimer, the term of this patent is extended or adjusted under 35 U.S.C. 154(b) by 90 days.

(21) Appl. No.: 10/130,983

(22) PCT Filed: Nov. 23, 2000

(86) PCT No.: PCT/SE00/02314

§ 371 (c)(1),
(2), (4) Date: May 24, 2002

(87) PCT Pub. No.: WO01/38563

PCT Pub. Date: May 31, 2001

(30) Foreign Application Priority Data

Nov. 24, 1999 (SE) .............................................. 9904254

(51) Int. Cl.[7] .............................. C12Q 1/18; C12Q 1/30; C12Q 1/02
(52) U.S. Cl. .............................. 435/32; 435/27; 435/29; 435/4
(58) Field of Search .............................. 435/27, 28, 29, 435/4

(56) References Cited

FOREIGN PATENT DOCUMENTS

| JP | 53-127880 | 11/1978 |
|----|-----------|---------|
| JP | 57-074095 | 5/1982 |
| JP | 50-15396 | 1/1993 |
| WO | WO 94/03632 | 2/1994 |

OTHER PUBLICATIONS

Shepherd et al, (Antimicrob. Agents Chemother; V.32(11), p.1693–1698(1998)Abstract Only.*

* cited by examiner

*Primary Examiner*—Louise N. Leary
(74) *Attorney, Agent, or Firm*—Young & Thompson

(57) ABSTRACT

The concentration or amount of living micro-organisms in a liquid sample can be determined in a reliable manner by determining the concentration of a substance, secreted by the micro-organisms, in the sample, which sample then is subjected to a treatment killing the micro-organisms; whereupon the concentration of the substance is measured anew. The relation between the first and second concentration is used as a measure of the concentration of micro-organisms in the sample.

8 Claims, 3 Drawing Sheets

METHOD FOR THE DETERMINATION OF THE CONCENTRATION OF MICROORGANISMS

Figure 1:
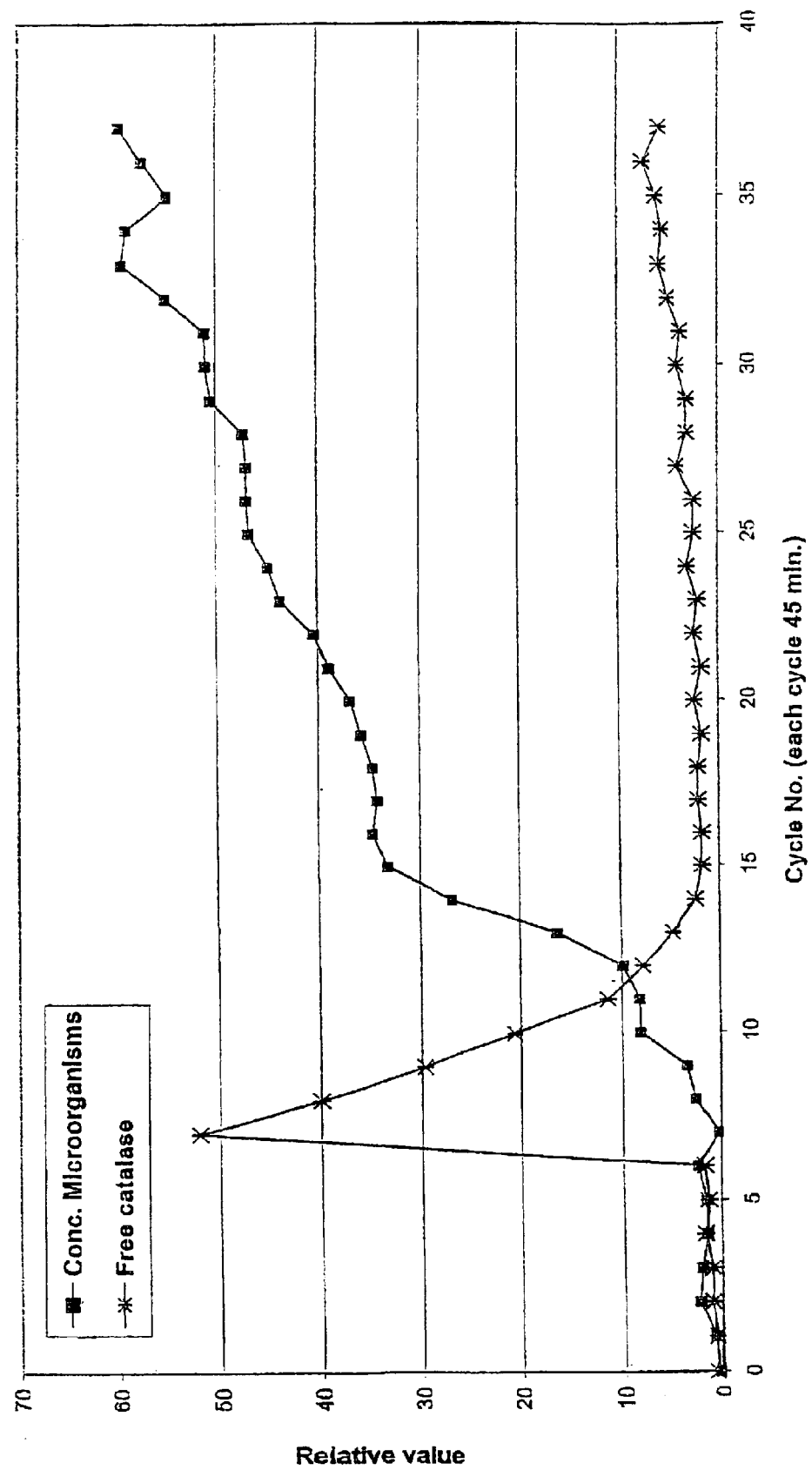

The present invention concerns a method for the determination of the amount of micro-organisms and/or biological activity in a sample. The invention primarily concerns the determination of the amount of aerobic micro-organisms in a fluid sample taken from a process fluid

BACKGROUND OF THE INVENTION

Micro-organisms are present practically everywhere and they exhibit an extraordinary power to adapt even to very hostile environments. It is important to be able to determine the amount of micro-organisms in process fluids and other solutions, e.g. in order to adjust the amount of process chemicals, to ensure that set limits are not exceeded, and in order to monitor processes. It is also important to be able to monitor the amount of micro-organisms, in order to quickly respond to changes. As examples of process fluids can be mentioned paper pulp and process fluids associated therewith, product flows and wash- and rinse liquids in food industry, municipal and industrial waste waters, fluids within other process industry, such as textile industry, water reservoirs, swimming pools etc.

The most frequently used method for determination of the concentration of micro-organisms and/or microbiological activity in fluids is based on counting the number of micro-organisms in a sample. Several methods are in use, of which the large majority are based on cultivating the micro-organisms in or on a medium, e.g. on agar plates or so called dipsticks. The cultivation requires a suitable environment and an incubation time between one to five days. The result is obtained after a manual or automated count of the number of visible colonies. It has however been shown, that in some cases more than 90% of the micro-organisms, originally present in the sample, die either at the time of sampling, during transport or during the incubation which favours certain strains. The reliability of these methods should therefor be questioned, both when it comes to the number and the type of micro-organisms present in the sample.

Another approach is to study a sample under microscope and count the number of micro-organisms. This also allows identification of different species, but this is work-intensive and requires good knowledge of both the method and micro-organisms. This method is probably the most reliable in clean nutrient solutions, but in process solutions which often consist of suspensions of particles, e.g. fibres, flocs or other finely dispersed material, practical difficulties arise. One problem is that dead micro-organisms have to be separated from living ones, something which often is performed with the aid of some colouring procedure. Another problem is that the micro-organisms often are attached to the particles, e.g. to the fibres in a fibre suspension. Therefor, a study of a filtrate does not give a fair picture of the amount of micro-organisms in the real process solution. For these reasons, among others, a determination using microscopy would only exceptionally be used for routine examination of process solutions.

Prior art methods for the determination of the amount or concentration of micro-organisms are accordingly associated with many problems, e.g. insufficient accuracy and reliability due to the micro-organisms dying at the time of sampling, transport and/or incubation of the samples; errors due to the sample not being representative for the process solution (e.g. a filtrate); requirements that the determination is performed by skilled personnel; work-intensive procedures; time-consuming incubations.

The present invention sets out to solve these problems, among others by making available a method which is rapid, suitable for automatisation, independent of the constitution of the process solution, requires minimal work effort and maintenance of the equipment. Further benefits of the invention will become apparent from the description and example.

CLOSEST PRIOR ART

The use of catalase activity as a measure of microbiological activity in different applications within the pulp and paper industry is Known (D. Y. Prasad, Tappi Jounal, January 1989, 135–137). The disclosed measurements where however done on filtrates and compared to conventional incubation of agar plates. Knowing the amount of micro-organisms removed by filtration and the unpredictability of incubation methods, the accuracy of the report's conclusions should be questioned.

A widely held point of view (see e.g. Y. Vemac et al. Progress in Paper Recycling, February 1999, 83–88) seems to be that the relation between the amount of micro-organisms and the catalase concentration is uncertain and varying, i.e. due to the availability of nutrients, self poisoning and death among the micro-organisms, and the variations in microbial flora between different plants for the production of pulp and/or paper.

A method for the detection of micro-organisms through the measurement of catalase activity is disclosed in WO 94/03632. The micro-organisms are allowed to convert a substrate, hydrogen peroxide, to oxygen and water over a controlled period of time under buffered conditions. At the end of this controlled period of time, the remaining substrate is determined eletrochemically by the peroxidase catalysed rupture of carbon-fluorine bonds from an organo-fluoro compound using a fluoride ion sensitive electrode.

There remains a need for a reliable, rapid and simple method for online determinations of the amount of living micro-organisms in process solutions, and in particular in process solutions with suspended particles or fibres. Prior art methods are not only less suited for use with process solutions, but also fail in distinguishing between living and dead micro-organisms.

SUMMARY OF THE INVENTION

The present invention aims primarily to make available a method which makes it possible to determine the amount and/or concentration of aerobic micro-organisms in any process solution, rapidly and reliably, and with reduced requirements with regard to the knowledge and work effort necessary from the part of the user. This is achieved through a method according to the attached claims, which method simultaneously solves the problems associated with the prior art methods.

According to the inventive method, the concentration of a substance secreted by micro-organisms, is determined in a sample, and the micro-organisms killed, whereupon the concentration of said substance is measured anew, and the relation between the first measured concentration and the second concentration is used a measure of the amount of living micro-organisms originally present in the sample.

SHORT DESCRIPTION OF THE DRAWINGS

Figure 2:
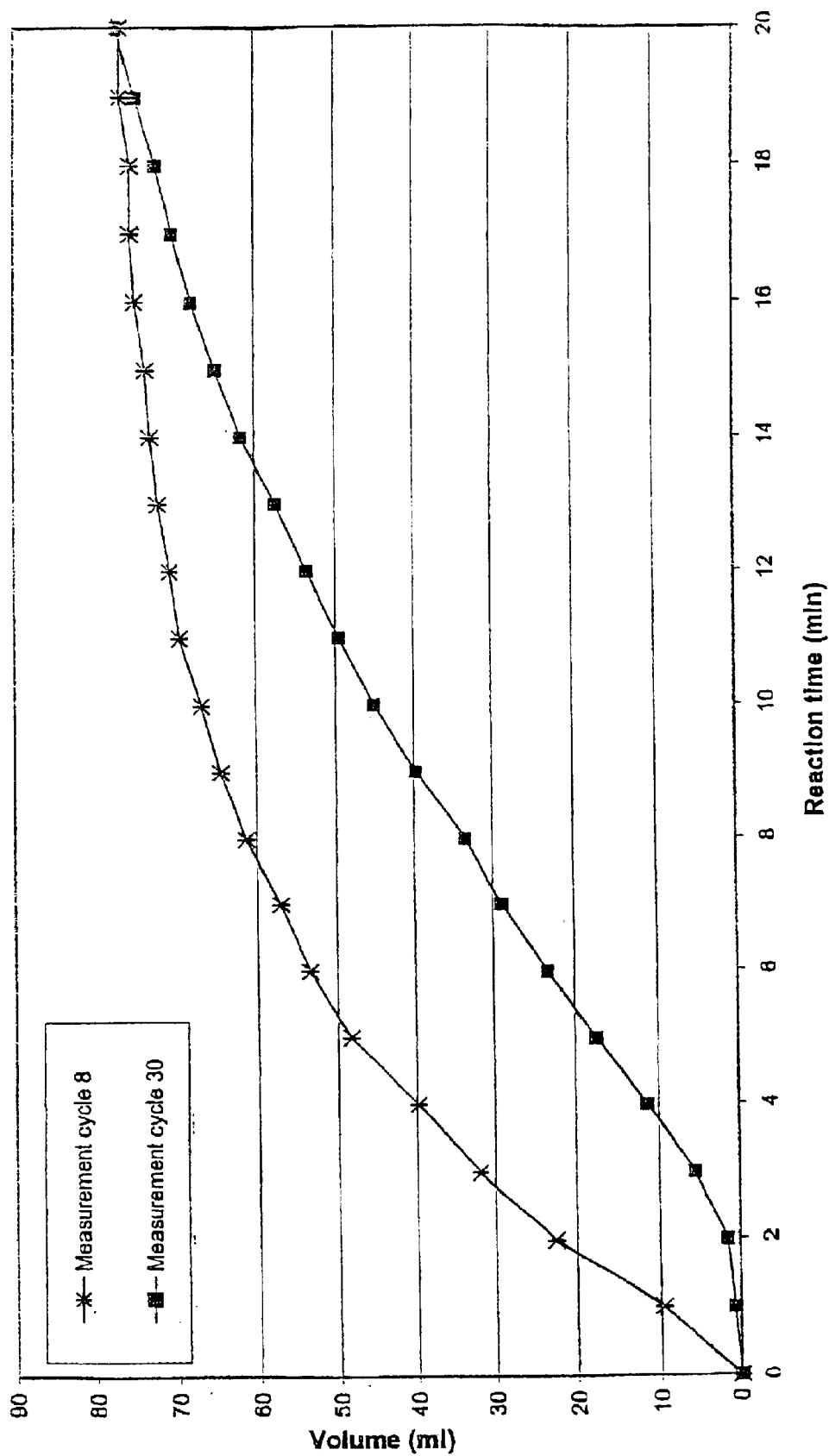
Figure 3:
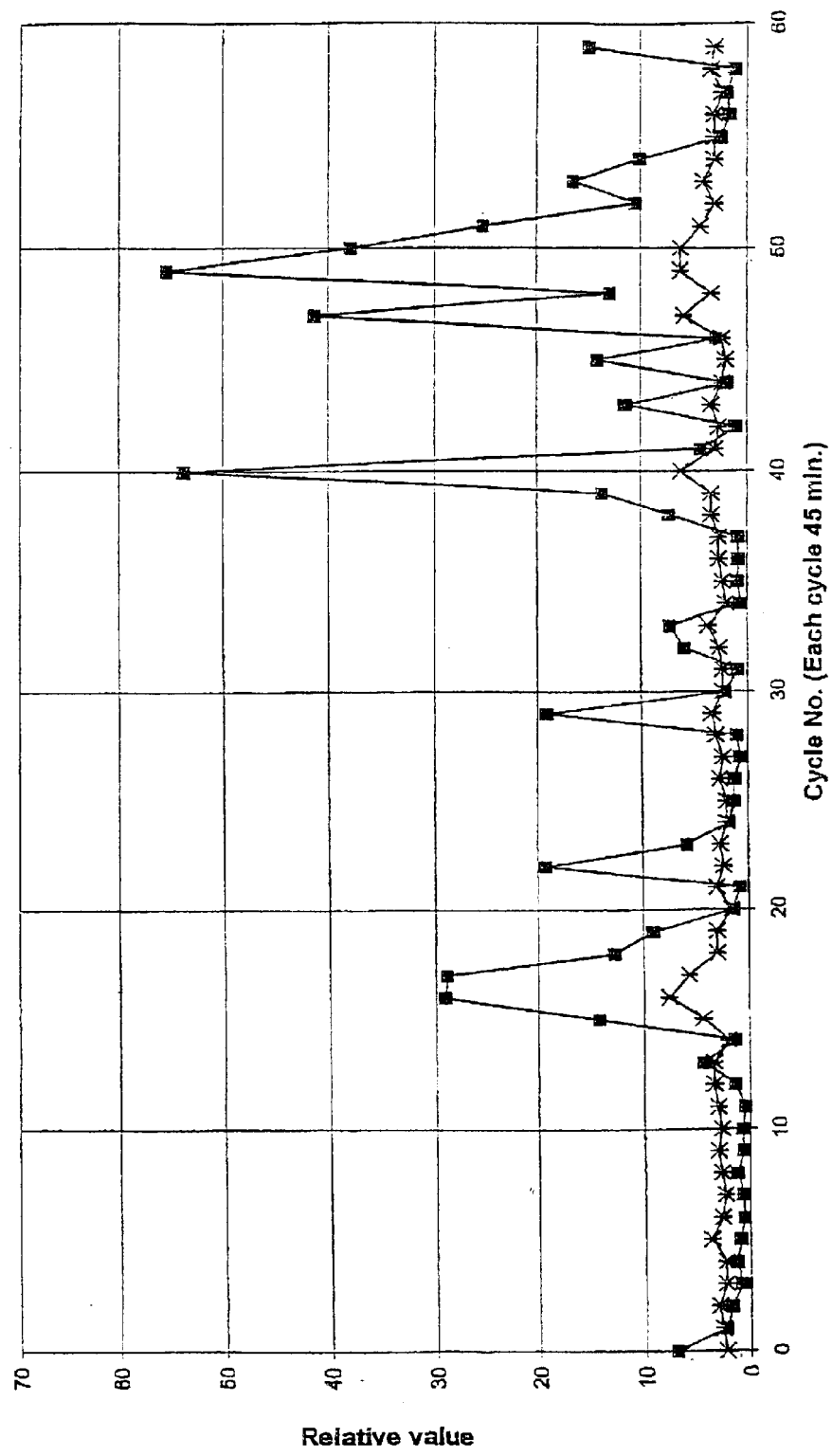

The invention will be described in the following description and non-limiting examples, with reference to the attached drawings, in which FIG. 1 is a diagram showing the concentration micro-organisms and free catalase, i.e. catalase which is not bound to living micro-organisms, during a test in a 1000 l tank;

FIG. 2 is a diagram showing the course of reaction for measurement cycle no. 8 and 30 of FIG. 1; and FIG. 3 is a dial showing the amount of micro-organisms and the concentration free catalase in practice, in the white water system of a plant for recycled fibres.

DESCRIPTION

Hydrogen peroxide is formed during the metabolism of aerobic and aerotolerant anaerobic micro-organisms. As a protection against the build-up of potentially lethal amounts of hydrogen peroxide, the micro-organisms synthesise the enzyme catalase, which together with the enzymes superoxide dismutase and peroxidase have an important role in the protection against the deleterious effects of an oxygen-mediated metabolism. Organisms that tolerate oxygen always contain superoxide dismutase but not always catalase. However, all hiterto known strictly anaerobic organisms lack both superoxide dismutase and catalase.

Within the pulp and paper industry, the use of chlorine bleaching has increasingly been replaced by the use of more environmentally friendly bleaching chemicals. Hydrogen peroxide is one of these chemicals.

The process flows in pulp and paper industry are not sterile. In particular the handling of recycled fibres gives a considerable contribution of micro-organisms. These can cause problems, in part by the formation of slime and sediment, in part because they contaminate the end-product, and in part through the enzymes excreted by the micro-organisms.

The closing of processes and use of filtrates aggravate these problems. It has been shown that the catalase excreted by micro-organisms in pulp suspensions, e.g. in recycled fibre suspensions, breaks down a noticeable part of the added hydrogen peroxide. FIG. 3 shows an example of how the catalase concentration varies in the white water at a pulp plant using recycled fibres.

It is therefor important both to be able to combat micro-organisms in these process flows and to consider the real amount, when dosing chemicals, both bleaching chemicals and biocides.

It has been shown that, when measuring the concentration of a substance, secreted by micro-organisms in a sample, which then is subjected to a treatment killing the micro-organisms, whereupon the concentration of said substance is measured anew, the relation between the first measured concentration and the second concentration can be used as a measure of the amount of living micro-organisms originally present in the sample. Further, the ways in which the concentration of said substance changes during and after killing of the micro-organisms, can give information about the type of micro-organisms present in the sample.

The present invention thus concerns a method for the determination of the amount or concentration of living micro-organisms in a fluid sample, such as a process liquid, characterized in that the concentration of a substance secreted by micro-organisms is measured in the sample, which sample is then subjected to a treatment killing the micro-organisms, whereupon the concentration of said substance is measured anew, and the relation between the first and second concentration is used as a measure of the concentration living micro-organisms present in the sample.

The treatment killing the micro-organisms can consist of a chemical treatment, e.g. the addition of a chemical substance in an amount sufficient to kill the micro-organisms, or a physical treatment, e.g. heating, electromagnetic radiation or ultra sound or other suitable treatments.

Preferably the measured substance is an enzyme and the treatment killing the enzymes is an addition of a biocide or comparable substance in an amount, sufficient to kill the micro-organisms.

According to a preferred embodiment, which is illustrated in FIG. 2, the concentration of a substance, e.g. catalase, is measured at several occasions during and after the treatment killing the micro-organisms, and the concentration is plotted against time and the resulting curve used as an indication of the type of micro-organisms. A slow increase of the concentration of the substance, e.g. catalase, indicates that the micro-organisms have a certain resistance towards the added biocide or the treatment meant to kill the micro-organisms. By collecting data for different types of micro-organisms identified using an independent method, e.g. microscopy, the inventive method can be calibrated. The speed of increase, e.g. for the catalase concentration, after commencing the treatment for killing the micro-organisms, e.g. an addition of hydrogen peroxide, gives information as to the type of micro-organisms. The total amount of the substance released gives information about the amount of living micro-organisms in the sample.

The treatment killing the micro-organisms can be the addition of a biocide, heating the sample, lyzing the micro-organisms in the sample etc. Preferably the micro-organisms are killed through the addition of a biocide, e.g. hydrogen peroxide. The use of hydrogen peroxide is particularly suitable in applications within the pulp and paper industry.

According to one embodiment of the invention, the measurement is conducted as follows: a sample is taken from a process flow without pre-treatment or with only slight pre-treatment, such as coarse filtration, homogenisation or separation of gas bubbles, and led into a measuring chamber. Into the measuring chamber a first, lesser amount of substrate e.g. hydrogen peroxide is added, and the amount of enzyme initially present in the sample, e.g. catalase, is calculated based on the production of gas when the hydrogen peroxide is broken down. Consequently a second, larger amount substrate e.g. hydrogen peroxide, is added in an amount sufficient to kill the micro-organisms present in the sample. The amount of enzyme, e.g. catalase liberated when the micro-organisms die, is measured at one or preferably several occasions until the value has stabilised. The total amount released enzyme gives information as the amount living micro-organisms present in the sample, and the speed with which the enzyme is liberated, gives information about the type of micro-organisms.

According to another embodiment, the sample is treated in the same way, but peroxide is added only once. The dose is adjusted so, that the biocidic property of hydrogen peroxide does not kill the micro-organisms until after about 2 to 5 minutes. The liberation of catalase from the micro-organisms will then go on for the entire measurement period, chosen to be 20 minutes. This embodiment does not offer as good possibilities for differentiating between different types of bacteria/micro-organisms, but is functionally more simple. This second embodiment has been used in the practical trials shown in the attached examples.

EXAMPLES

Example 1

Determination Of the Concentration Aerobic Micro-Organisms And Free Catalase In White Water from a Pulp And Paper Plant Using Recycled Fibre Experimental apparatus: An experimental apparatus for observation of the catalase concentration was assembled in order to test the invention. Both the amount of free catalase, which initially is not included in micro-organisms and the amount of micro-organisms was indicated. This apparatus used catalase as the substance secreted by the micro-organisms and used hydrogen peroxide both for the determination of the catalase concentration and as the biocide. Mainly the decomposition of hydrogen peroxide which takes place at an early stage was used for determining the concentration free catalase, and the speed of decomposition after the hydrogen peroxide had acted as biocide, was used to give the concentration of micro-organisms.

Bacteria culture: The culture of micro-organisms in the form of bacteria was done in a 10001 tank. The tank was filled with white water from a deinking plant at a pulp and paper plant using recycled fibre, and the solution contained normal amounts of fibre and filler. The solution is in the following referred to as "water". The amount of micro-organisms was lowered to almost zero by an addition of peroxide. The tank was left to stand for about 12 hours, which resulted in that the natural decomposition of catalase in a water of this type gave a catalase concentation of almost zero. Water from the cultivation tank was automatically pumped to the test apparatus at 45 minute intervals.

Oxygen and nutrients: The nutrient content of the water is ample and non-limiting for a period as short as the present experiment. The availability of oxygen is very high at the start of the experiment, as the water becomes saturated with oxygen from the decomposition of the peroxide used for sterilisation. This means that the natural partial pressure of nitrogen in the water is replaced by oxygen, which results in an oxygen concentration about four times as high as in water saturated with air. The continuous oxygenation of the water was achieved by circulating the water by pumping it and releasing it above surface, resulting in a normalisation of the oxygen concentration to a level corresponding to normal air saturation later in the experiment Result: The result is shown in the diagram of FIG. 1, where a relative value for the amount of micro-organisms and the concentration free catalase has been determined in a total of 37 measurement cycles. In the following, the result of different measurement cycles is explained:

Measurement cycle 0: Starting position for the experiment. Low concentration bacteria and free catalase. The water contains about 15 ppm hydrogen peroxide.

Measurement cycle 2: Addition of 50l water containing bacteria. The bacteria are killed or inactivated by the hydrogen peroxide in the water.

Measurement cycle 7: Free commercial catalase has been added in order to remove the hydrogen peroxide present in the water up to this point. This triggers the growth of bacteria, at the same time as it gives the possibility to study the degradation of the added free catalase in the system. The concentration of bacteria measured with a "dipstick" is <$10^1$ cfu/ml.

Measurement cycle 8: This measurement cycle is taken as an example of a point where the concentration free catalase is high and the concentration bacteria is low. The course of the reaction in the experimental apparatus upon addition of hydrogen peroxide to the water sample is shown in the diagram of FIG. 2, showing the course of reaction for measurement cycles 8 and 30. See also the comments to this diagram.

Measurement cycle 7–15: Bacterial growth phase, where the growth is promoted by the high partial pressure of oxygen in the starting phase. Probably certain types of bacteria are favoured by the high oxygen concentration.

Measurement cycle 16–18: The high oxygen surplus has now been consumed. The bacteria previously favoured die to a degree and an adaptation to lower availability of oxygen takes place.

Measurement cycle 19–33: A growth phase with constant supply of oxygen due to the circulating water being released above surface in the cultivation tank. In the final phase, the added oxygen is consumed at a pace resulting in a decrease and other bacteria with higher catalase content are favoured.

Measurement cycle 30: This measurement cycle is taken as an example of a situation where the concentration free catalase is low and the bacterial concentration high. The course of reaction when hydrogen peroxide is added to the water sample is shown in the diagram of FIG. 2, showing the course of reaction for measurement cycles 8 and 30. See also the comments to this diagram.

Measurement cycle 33: The bacterial concentration measured with a "dipstick" is about $10^6$ cfu/ml.

Measurement cycle 34–35: A low concentration of a biocide with a degradation time of a couple of measurement cycles is added before cycle 34. This gives as expected a decreased bacterial concentration and an increase of the free catalase.

Measurement cycle 36–37: The biocide action has ceased and the growth starts again. The concentration free catalase is reduced as it is decomposed at the same time as a lesser amount is liberated from killed bacteria.

The course of reaction for the measurement cycles 8 and 30 is shown in the diagram of FIG. 2. The degradation of hydrogen peroxide which initially takes place is used to determine the concentration free catalase, and the speed of degradation after the added hydrogen peroxide has started to act as a biocide gives the concentration of micro-organisms. Both cases have been chosen so, that the reaction results in the same volume in ml after 20 minutes.

Dosed amount: The amount peroxide added corresponds to a liberated amount of about 130 ml, and it is not, in any of the cases, the peroxide concentration which dominates the decease in reaction speed but the decomposition of available catalase.

Example 2

Micro-Organisms And Free Catalase In the White Water System Of a Plant for Recycled Fibres During Normal Use The experimental apparatus described for evaluation of the invention and used for observing the bacterial growth in the culture described in Example 1 was directly connected to the white water system of a deinking plant and used to observe the concentration free catalase and micro-organisms.

The peak values of micro-organisms concentration are due to the transfer of filtrates from a buffer tank, containing high concentration bacterial, to the white water. The organisms from the buffer solution are killed when they are pumped from the peroxide free buffer tank into the white water where hydrogen peroxide is dosed and acts both as bleaching chemical and biocide.

Different process waters, more or less contaminated by micro-organisms, enter the white water, and depending of the particular flow, varying concentrations of bacteria are achieved. The fast and large variations in the concentration of micro-organisms are not directly corresponding to the amount free catalase, although a correlation certainly exists.

Different reference measurements give different results and the method according to the present invention has great flexibility when it comes to the mathematical adaptation of the measurement values which form the basis for the out-signal. This mews that a reference system must be chosen and in the present case, so called dipsticks were used as reference. A good correlation with dipstick values was achieved where the relative concentration micro-organisms is indicated and 0 corresponds to $10^0$ cfu/ml, 10 corresponds to $10^1$ cfu/ml, 40 corresponds to $10_4$ cfu/ml, and 50 corresponds to $10^5$ cfu/ml.

Different calibrations for different applications are however possible within the scope of the invention Although the invention has been described with regard to its preferred embodiments, which constitute the best mode presently known to the inventors, it should be understood that various changes and modifications as would be obvious to one having the ordinary skill in this art may be made without departing from the scope of the invention as set forth in the claims appended hereto.

What is claimed is:

1. Method for the determination of the concentration living micro-organisms in a sample, characterized in that the concentration of a substance secreted by the micro-organisms is measured in the sample, which sample then is subjected to a treatment killing the micro-organisms, whereupon the concentration of said substance is determined anew, and the relation between the first and the second concentration is used as a measure of the concentration living micro-organisms in the sample.

2. Method according to claim 1, characterized in that the treatment killing the micro-organisms comprises the addition of a biocide.

3. Method according to claim 1, characterized in that the measured substance is an enzyme.

4. Method according to claim 3, characterized in that the measured substance is catalase and the treatment killing the micro-organisms is an addition of a biocide.

5. Method according to claim 4, characterized in that the biocide is hydrogen peroxide.

6. Method according to claim 1, characterized in that the concentration substance is measured on several occasions during and after the treatment killing the micro-organisms and that the concentration as a function of time is used as an indication of the type of micro-organisms.

7. A method for the determination of the concentration of living micro-organisms in a sample, characterized in that the concentration of a substance secreted by the micro-organisms is measured in the sample, which sample then is subjected to a treatment killing the micro-organisms, whereupon the concentration of said substance is determined anew, and the relation between the first and the second concentration is used as a measure of the concentration living micro-organisms in the sample, and wherein the treatment killing the micro-organisms comprises a treatment with electromagnetic radiation.

8. A method for the determination of the concentration of living micro-organisms in a sample, characterized in that the concentration of a substance secreted by the micro-organisms is measured in the sample, which sample then is subjected to a treatment killing the micro-organisms, whereupon the concentration of said substance is determined anew, and the relation between the first and the second concentration is used as a measure of the concentration living micro-organisms in the sample, wherein the sample is a liquid sample taken from a process flow without prior filtration.

* * * * *